US008748358B2

(12) United States Patent
Koshima et al.

(10) Patent No.: US 8,748,358 B2
(45) Date of Patent: Jun. 10, 2014

(54) LUBRICATING OIL ADDITIVE, LUBRICATING OIL COMPOSITION CONTAINING THE SAME, VARIOUS LOW-FRICTION SLIDING MEMBERS, ROLLING BEARING, AND SLIDING BEARING

(75) Inventors: Hiroaki Koshima, Sodegaura (JP); Hideki Kamano, Ichihara (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 1044 days.

(21) Appl. No.: 12/294,457

(22) PCT Filed: Mar. 16, 2007

(86) PCT No.: PCT/JP2007/055387
§ 371 (c)(1),
(2), (4) Date: Sep. 25, 2008

(87) PCT Pub. No.: WO2007/119400
PCT Pub. Date: Oct. 25, 2007

(65) Prior Publication Data
US 2010/0234254 A1 Sep. 16, 2010

(30) Foreign Application Priority Data
Mar. 31, 2006 (JP) ................................. 2006-097203

(51) Int. Cl.
*C10M 133/44* (2006.01)
*C07D 249/08* (2006.01)

(52) U.S. Cl.
CPC ....... *C10M 133/44* (2013.01); *C10M 2215/223* (2013.01); *C10N 2240/02* (2013.01); *C07D 249/08* (2013.01)
USPC ........................................ 508/257; 548/262.2

(58) Field of Classification Search
USPC ........................................ 508/257; 548/262.2
See application file for complete search history.

(56) References Cited

U.S. PATENT DOCUMENTS

| 2,497,839 | A | | 2/1950 | Ralston et al. |
| 3,047,498 | A | | 7/1962 | McGrath et al. |
| 4,115,288 | A | * | 9/1978 | Schmitt .......................... 508/279 |
| 4,189,587 | A | | 2/1980 | Holt et al. |
| 4,257,779 | A | | 3/1981 | Sung et al. |
| 4,285,823 | A | | 8/1981 | Sung et al. |
| 4,375,420 | A | * | 3/1983 | Knollmueller et al. ...... 252/78.3 |
| 4,392,968 | A | | 7/1983 | Ishida et al. |
| 4,734,209 | A | | 3/1988 | Phillips et al. |
| 4,874,579 | A | | 10/1989 | Schmid et al. |
| 4,948,523 | A | * | 8/1990 | Hutchison et al. ............ 508/273 |
| 5,482,521 | A | | 1/1996 | Avery et al. |
| 5,912,212 | A | * | 6/1999 | Igarashi et al. ................ 508/275 |
| 5,997,593 | A | | 12/1999 | McDonnell et al. |
| 6,303,547 | B1 | | 10/2001 | Balasubramaniam |
| 6,573,223 | B1 | * | 6/2003 | Vinci .............................. 508/192 |
| 6,861,395 | B2 | * | 3/2005 | Eastwood et al. ............. 508/275 |
| 2004/0038835 | A1 | | 2/2004 | Chasan et al. |
| 2004/0092405 | A1 | | 5/2004 | Konishi et al. |
| 2005/0213854 | A1 | | 9/2005 | Konishi et al. |
| 2006/0263604 | A1 | * | 11/2006 | Martin et al. .................. 428/408 |

FOREIGN PATENT DOCUMENTS

| EP | 1 338 641 | 8/2003 |
| GB | 1 111 680 | 5/1968 |
| JP | 63 10699 | 1/1988 |
| JP | 64 29497 | 1/1989 |
| JP | 02 049096 | 2/1990 |
| JP | 02 049097 | 2/1990 |
| JP | 6 100881 | 4/1994 |
| JP | 6 157471 | 6/1994 |
| JP | 7 506860 | 7/1995 |
| JP | 8 165483 | 6/1996 |
| JP | 10-212275 | 8/1998 |
| JP | 2002 534436 | 10/2002 |
| JP | 2003 505577 | 2/2003 |
| JP | 2003 074557 | 3/2003 |
| JP | 2003 238982 | 8/2003 |
| JP | 2004 315703 | 11/2004 |
| JP | 2004 331950 | 11/2004 |
| JP | 3650635 | 2/2005 |
| JP | 2005 054037 | 3/2005 |
| JP | 2005 60416 | 3/2005 |
| WO | WO 2005014761 A2 * | 2/2005 |
| WO | 2005 080305 | 9/2005 |
| WO | 2006/115666 A1 | 11/2006 |

OTHER PUBLICATIONS

Ren, T. et al., "The Effect of Molecular Structure of N-Containing Heterocyclic Compounds on their Wear Properties", Lubrication Science, vol. 5, No. 3, pp. 205-212, (1993).
U.S. Appl. No. 12/672,108, filed Feb. 4, 2010, Kamano, et al.
M. Kano, et al. "The Effect of ZDDP and MODTC Additives on Friction Properties of DLC and Steel Cam Follower in Engine Oil", $2^{nd}$ World Tribology Congress, Sep. 3-7, 2001, 1 cover Page and p. 342.
Supplementary Partial European Search Report issued Mar. 14, 2014, in European Patent Application No. 07738832.0 filed Mar. 16, 2007.
Wei, et al., Lubrication Science, vol. 4, No. 3, pp. 219-232, XP007910996 (1992).
Miller, Journal of the Institute of Petroleum, vol. 59, No. 565, pp. 27-31 (1973).
He, et al., Tribology Letters, vol. 13, No. 2, pp. 87-93, XP003024589 (2002).

* cited by examiner

*Primary Examiner* — James Goloboy
(74) *Attorney, Agent, or Firm* — Oblon, Spivak, McClelland, Maier & Neustadt, L.L.P.

(57) ABSTRACT

Provided is an additive for lubricating oils which enhances frictional characteristics of slide parts in internal combustion engines and driving system transmission engines and which exhibit an excellent fuel consumption reducing effect. The above additive for lubricating oils comprises a heterocyclic compound having a heterocyclic skeleton originating in a compound selected from pyridines, pyrroles, pyrimidines, pyrazoles, pyridazines, indazoles, pyrazines, triazines, triazoles, tetrazoles, oxazoles, oxadiazoles, thiazoles, thiadiazoles, furans, dioxanes, pyrans and thiophenes. A lubricating oil composition containing the above additive for lubricating oils is effectively used for various low friction slide members, antifriction bearings and slide bearings.

14 Claims, No Drawings

LUBRICATING OIL ADDITIVE, LUBRICATING OIL COMPOSITION CONTAINING THE SAME, VARIOUS LOW-FRICTION SLIDING MEMBERS, ROLLING BEARING, AND SLIDING BEARING

BACKGROUND OF THE INVENTION

The present invention relates to an additive for lubricating oils, a lubricating oil composition containing the same, various low friction slide members, an antifriction bearing and a slide bearing. More specifically, the present invention relates to an additive for lubricating oils used for a part to be lubricated in which a low friction slide members such as an inorganic material for being coated, a lubricating oil composition containing the same, various low friction slide members which have a diamond-like carbon film at least on a part of a slide part and in which the above lubricating oil composition is used for a sliding surface, an antifriction bearing and a slide bearing.

RELATED ART

In recent years, environmental problems in a global scale such as global warming and ozone depletion draw large attentions. In particular, attentions are paid to a reduction in carbon dioxide which is considered to exert a large effect on global warming of the whole earth. In order to reduce carbon dioxide, requirement of countermeasures for a reduction in fuel consumption to the automotive industry is increased, and among the countermeasures, lubricating oils play a very large role.

It is tried as countermeasures for a reduction in fuel consumption in lubricating oils to (1) reduce a viscosity resistance and a stirring resistance in a fluid lubrication area by reducing a viscosity of lubricating oils and (2) reduce a frictional loss in a boundary lubrication area by blending an optimum friction reducing agent and various additives.

Various researches for friction reducing agents have been made with a central focus on organic molybdenum compounds such as MoDTC, MoDTP and the like (for example, Patent document 1). The organic molybdenum compounds are very excellent in a friction reducing effect when a lubricating oil is fresh but inferior in continuity, and in addition thereto, involved therein is the defect that the performances thereof can not be exhibited under the presence of soot produced when the lubricating oil is deteriorated. Further, compounds containing metals and phosphorus cause clogging of a filter in an exhaust gas refining equipment and catalyst poisoning. Accordingly, strongly desired are friction reducing agents which exhibit continually performances thereof even under the presence of soot and which do not contain metals and phosphorus and are an ashless type.

On the other hand, an application example of heterocyclic compounds to lubricating oils is shown in Patent document 2, wherein benzotriazole is applied as a corrosion inhibitor. It is described in Patent document 3 to apply benzotriazole derivatives to a freezing machine oil composition, and an effect of an abrasion resistance is asserted therein. It is shown in Patent document 4 that imidazole fluorine derivatives are used as a surface treating agent. It is described in Patent document 5 to use polybenzimidazole as a polymer having an internal lubricant. Fluid compositions for an active suspension which contain thiadiazole and benzotriazole and which are excellent in an abrasion resistance are described in Patent document 6. It is described in Patent document 7 to use triazine derivatives as a lubricating oil or a dispersant for fuels. Indazolethione additives as a lubricating oil are described in Patent document 8. Low tractional fluids having a triazine structure are described in Patent document 9.

Lubricating oil compositions containing triazine derivatives are described in Patent document 10.

However, additives for lubricating oils having a friction reducing characteristic and a fuel consumption reducing effect are not described in any one of the Patent documents described above.

On the other hand, hard thin film materials are expedited to be applied recently as a surface treating technique for parts exposed to severe friction and abrasion environment. Various coating materials such as diamond-like carbon (DLC), titanium nitride (TiN), chromium nitride (CrN) and the like are investigated, and particularly DLC coating materials have an excellent low friction characteristic and are expected as a low friction slide member.

However, it is reported that if a lubricating oil composition containing an organic molybdenum compound is applied to a slide part comprising a DLC coating material, a friction reducing effect is not sufficiently exhibited (non-patent document 1).

Further, fatty acid ester based-ashless friction controlling agents and aliphatic amine based-ashless abrasion inhibitors are described in a patent document 11. The above controlling agents and inhibitors display a friction reducing effect to DLC coating materials but do not display a satisfactory effect to between steels. Usually, slide parts coated with DLC which are not assumed to be a slide part is present in a mixed form in one apparatus, and therefore additives which exhibit a friction reducing effect not only to slide parts coated with DLC but also between steels are desired.

Patent document 1: Japanese Patent No. 3650635
Patent document 2: JP 1989 29497A
Patent document 3: JP 1994 100881A
Patent document 4: JP 1994 157471A
Patent document 5: JP 1995 506860A
Patent document 6: JP 1996 165483A
Patent document 7: JP (through PCT) 2002 534436A
Patent document 8: JP (through PCT) 2003 505577A
Patent document 9: JP 2004 315703A
Patent document 10: JP 2004 331950A
Patent document 11: JP 2003 238982A
Non-patent document 1: Kano et al., "World Tribology Congress", 2001.9, Vienna, Proceeding p. 342

DISCLOSURE OF THE INVENTION

Problems to be Solved by the Invention

An object of the present invention is to provide an additive for lubricating oils which exhibits a friction reducing effect not only to slide parts coated with DLC but also to sliding between steels and sliding of steel with aluminum and which is useful as an ashless friction reducing agent, a lubricating oil composition containing the same, various low friction slide members which are prepared by using the above lubricating oil composition and have a DLC film, an antifriction bearing and a slide bearing.

Means for Solving the Problems

In light of the existing situation of the conventional techniques described above, researches carried out by the present inventors in order to develop a lubricating oil composition which enhances a frictional characteristic in a slide member have resulted in finding that a heterocyclic compound having a specific chemical structure shows excellent characteristics as a friction reducing agent and can provide a fuel consumption saving performance in internal combustion engines and driving system transmission engines, and thus the present inventors have completed the present invention.

That is, the present invention provides the following (1) to (14):

(1) An additive for lubricating oils comprising a heterocyclic compound represented by the following general formula (I):

[Chemical formula 1]

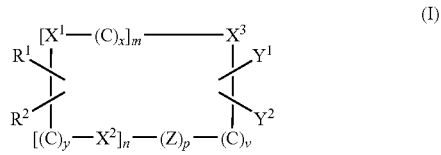

(I)

[in the general formula (I), $X^1$, $X^2$ and $X^3$ represent at least one element selected from "N" or "NH" ("N" is nitrogen), "O" (oxygen) and "S" (sulfur), and they each may be different kinds of the elements; $(C)_x$, $(C)_y$ and $(C)_v$ represent an alkylene group or a residue of an alkylene group substituted with one or two groups of $R^1$, $R^2$ or $Y^1$ and $Y^2$; "x" and "y" are an integer of 0 to 2, and "v" is an integer of 0 to 5 (as described later, when "p" is 1, "v" is an integer of 0 to 3); "m" and "n" are 0 or 1, and "m", "n" and "v" are not 0 at the same time; $R^1$ and $R^2$ each represent a hydrogen atom or a group selected from an alkyl group having 6 to 30 carbon atoms, an alkenyl group, an alkyl and alkenyl amino group, an alkyl and alkenyl amide group, an alkyl and alkenyl ether group, an alkyl and alkenyl carboxyl group, a cycloalkyl group and an aryl group; $R^1$ and $R^2$ may be the same or different, and when "p" is 0, $R^1$ and $R^2$ are not a hydrogen atom at the same time; $Y^1$ and $Y^2$ represent a hydrogen atom or a functional group selected from a hydrocarbon residue, an amino group, an amide group, a hydroxyl group, a carbonyl group, an aldehyde group, a carboxyl group, an ester group, an ether group and a halogen atom or a hydrocarbon residue containing the above functional group or a group obtained by adding the hydrocarbon residue containing the above functional group to the above functional group; "Z" represents the following structural unit (II), and "p" is 0 or 1;

[Chemical formula 2]

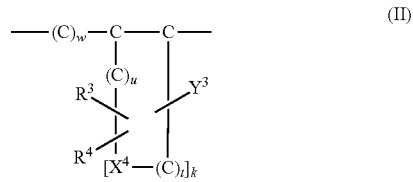

(II)

$X^4$ represents any element selected from "N" or "NH" ("N" is nitrogen), "O" (oxygen) and "S" (sulfur); $(C)_w$, $(C)_u$ and $(C)_t$ represent an alkylene group or a residue of an alkylene group substituted with $R^3$, $R^4$ or $Y^3$; "w" is an integer of 0 to 2; "u" is an integer of 0 to 4; "k" is an integer of 0 to 2; "t" is an integer of 0 to 3; when "p" is 1, "v" is an integer of 0 to 3; $R^3$ and $R^4$ may be the same or different, and $R^1$, $R^2$, $R^3$ and $R^4$ are not a hydrogen atom at the same time; $Y^3$ represents a hydrogen atom or a functional group selected from a hydrocarbon residue, an amino group, an amide group, a hydroxyl group, a carbonyl group, an aldehyde group, a carboxyl group, an ester group, an ether group and a halogen atom or a hydrocarbon residue containing the above functional group; and cyclic parts in the general formula (I) and the structural unit (II) may have a double bond].

(2) The additive for lubricating oils as described in the above item (1), wherein "p" in the general formula (I) is 0, and $X^1$, $X^2$, $X^3$ and $X^4$ are either element selected from "N" (nitrogen) or "O" (oxygen).

(3) The additive for lubricating oils as described in the above item (1), wherein p in the general formula (I) is 1, and $X^1$, $X^2$, $X^3$ and $X^4$ are either element selected from "N" (nitrogen) or "O" (oxygen).

(4) The additive for lubricating oils as described in any one of the above items (1) to (3), wherein the compound represented by the general formula (I) has a heterocyclic skeleton originating in a compound selected from pyridines, pyrroles, pyrimidines, pyrazoles, pyridazines, indazoles, pyrazines, triazines, triazoles, tetrazoles, oxazoles, oxadiazoles, thiazoles, thiadiazoles, furans, dioxanes, pyrans and thiophenes.

(5) The additive for lubricating oils as described in any one of the above items (1) to (4), wherein it is a friction reducing agent.

(6) A lubricating oil composition characterized by containing the additive for lubricating oils as described in any one of the above items (1) to (5) and a lubricating base oil.

(7) The lubricating oil composition as described in the above item (6), wherein it is used for internal combustion engines.

(8) The lubricating oil composition as described in the above item (6), wherein it is used for driving systems.

(9) The lubricating oil composition as described in any one of the above items (6) to (8), wherein it is used for low friction slide members used on a wet condition.

(10) The lubricating oil composition as described in the above item (9), wherein the low friction slide member is a member having a diamond-like carbon film on a surface.

(11) The lubricating oil composition as described in the above item (10), wherein the diamond-like carbon film comprises an amorphous carbon based-material having a hydrogen content of 30 atom % or less.

(12) A low friction slide member which is provided at least on a part of a slide part with a diamond-like carbon film and in which the lubricating oil composition as described in the above item (6) is used for a sliding surface, wherein it is selected from low friction slide members for internal combustion engines, low friction slide members for automatic transmissions, low friction slide members for infinitely variable transmissions, low friction slide members for manual transmissions, low friction slide members for an electric power steering, low friction slide members for shock absorbers for cars, low friction slide members for cooling medium compressors, low friction slide members for hydraulic pumps and low friction slide members for clutch pulleys.

(13) An antifriction bearing characterized by providing at least a part of a slide part with a diamond-like carbon film and using the lubricating oil composition as described in the above item (6) for a sliding surface.

(14) A slide bearing characterized by providing at least a part of a slide part with a diamond-like carbon film and using the lubricating oil composition as described in the above item (6) for a sliding surface.

Effect By The Invention

Use of the lubricating oil composition containing the additive for lubricating oils of the present invention makes it possible, for example, to enhance frictional characteristics of slide parts in internal combustion engines and driving system transmission engines and achieve an excellent fuel consumption reducing effect. In particular, when the lubricating oil composition of the present invention is applied to low friction slide members used under a wet condition, the fuel consumption reducing effect is displayed.

BEST MODE FOR CARRYING OUT THE INVENTION

Hereinafter, the present invention is explained in details.

The additive for lubricating oils of the present invention comprises the heterocyclic compound represented by the general formula (I) described above.

In the general formula (I) described above, "Z" represents the structural unit (II) described above, and "p" is 0 or 1.

When "p" is 0 and when any or all of $X^1$ to $X^3$ is "N", one of two bonding sites in respective "N" is occasionally a double bond. Shown is the state that one of $R^1$ and $R^2$ and one of $Y^1$ and $Y^2$ are bonded to "N" in which both bonding sites are single bonds or one hydrogen is bonded thereto.

All of "C" represent carbon elements, and either one of two bonding sites in respective "C" is occasionally a double bond. When "p" is 0, shown is the state that in both of a case where one bonding site of "C" is a double bond and a case where it does not have a double bond, expression of bonding sites of remaining one or two single bonds of "C" is abbreviated; expression of bonding sites of remaining two single bonds of "C" is abbreviated; and one group selected from $R^1$, $R^2$, $Y^1$ and $Y^2$ is bonded to the abbreviated bonding site. When "p" is 1, the same condition as in a case where "p" is 0 applies to $X^1$ to $X^3$, and when $X^4$ is "N", one of two bonding sites in "N" is occasionally a double bond. When both bonding sites are a single bond, shown is the state that one group selected from $R^3$, $R^4$, $Y^3$ and hydrogen is bonded thereto. When "p" is 1, the same condition as in a case where "p" is 0 applies to "C" in the general formula (I). All of "C" in the structural unit (II) represent a carbon element, and either one of two bonding sites in respective "C" is occasionally a double bond. Shown is the state that in both of a case where one bonding site of "C" is a double bond and a case where it does not have a double bond, expression of bonding sites of remaining one or two single bonds is abbreviated and that two groups selected from $R^3$, $R^4$, $Y^3$ and hydrogen are bonded to the abbreviated bonding sites. $R^1$, $R^2$, $R^3$ and $R^4$ each are a hydrogen atom or a group selected from an alkyl group having 6 to 30 carbon atoms, an alkenyl group, an alkyl or alkenyl amino group, an alkyl or alkenyl amide group, an alkyl or alkenyl ether group, an alkyl or alkenyl carboxyl group, a cycloalkyl group and an aryl group. $R^1$, $R^2$, $R^3$ and $R^4$ may be the same or different, and $R^1$ and $R^2$ and $R^3$ and $R^4$ are not a hydrogen atom at the same time. $Y^1$, $Y^2$ and $Y^3$ are a hydrogen atom or a functional group selected from a hydrocarbon residue, an amino group, an amide group, a hydroxyl group, a carbonyl group, an aldehyde group, a carboxyl group, an ester group, an ether group and a halogen atom or a hydrocarbon residue containing the above functional group or a group obtained by adding the hydrocarbon residue containing the above functional group to the above functional, and they may be the same or different.

(1) Case where "p" is 0:

The terms "m" and "n" are 0 or 1; "v" is an integer of 0 to 5; and "y" is an integer of 0 to 2. From the viewpoint of a stability of the compound, preferably, when "m" and "n" are 0, "v" is 4 or 5; when either of "m" and "n" is 0, "v" is 2 or 3; and when "m" and "n" are 1, "v" is 0 or 1. More preferably, when "m" and "n" are 0, "v" is 4 or 5; when "m" is 1 and "n" is 0 and when "v" is 2 or 3, "x" is 1 or 2; when "m" is 0 and "n" is 1 and when "v" is 2 or 3, "y" is 1 or 2; when "m" and "n" are 1 and when "v" is 0, "x" and "y" are 1 or "x" is 1, "y" is 2 or "x" is 2, "y" is 1; when "m" and "n" are 1 and when v is 1, "x" is 0, "y" is 1 or 2 or "x" is 1 or 2, "y" is 0 or "x" and y are 1.

$X^1$, $X^2$ and $X^3$ represent at least one element selected from "N" (nitrogen), "O" (oxygen) and "S" (sulfur), and from the viewpoints of a stability of the compound, a deterioration resistance of a product containing the compound and protecting the catalyst from being poisoned, $X^1$, $X^2$ and $X^3$ are preferably either element selected from "N" or "O" (oxygen).

When any or all of $X^1$, $X^2$ and $X^3$ are "N", one of two bonding sites in respective "N" is occasionally a double bond. When both bonding sites are single bonds, shown is the state that one of $R^1$, $R^2$ and $Y^1$ is bonded thereto or one group selected from hydrogen is bonded thereto.

All of "C" represent carbon elements, and any one of two bonding sites in respective "C" is occasionally a double bond. Shown is the state that in both of a case where one bonding site of "C" is a double bond and a case where it does not have a double bond, expression of bonding sites of remaining one or two single bonds is abbreviated and that one group selected from $R^1$, $R^2$, $Y^1$, $Y^2$ and hydrogen is bonded to the abbreviated bonding site.

$R^1$ and $R^2$ each are a hydrogen atom or a group selected from an alkyl group having 6 to 30 carbon atoms, an alkenyl group, an alkyl or alkenyl amino group, an alkyl or alkenyl amide group, an alkyl or alkenyl ether group, an alkyl or alkenyl carboxyl group, a cycloalkyl group and an aryl group. $R^1$ and $R^2$ may be the same or different, and $R^1$ and $R^2$ are not a hydrogen atom at the same time.

The alkyl group and the like are provided with 6 or more carbon atoms, whereby obtained is the compound which is endowed with a satisfactory solubility in a lubricating base oil and which has an excellent friction reducing effect, and they are provided with 30 or less carbon atoms, whereby the compound having an excellent friction reducing effect is obtained.

$R^1$ and $R^2$ are preferably a hydrogen atom or a hydrocarbon group having 12 to 24 carbon atoms, and to be specific, they are an alkyl group or alkenyl group having up to 24 carbon atoms such as octyl, octenyl, decyl, decenyl, dodecyl, dodecenyl, tetradecene, tetradecenyl, hexadecene, hexadecenyl, octadecyl, octadecenyl, oleyl, stearyl, isostearyl and the like, and they may be linear or branched.

$Y^1$ and $Y^2$ are a hydrogen atom or a functional group selected from a hydrocarbon residue, an amino group, an amide group, a hydroxyl group, a carbonyl group, an aldehyde group, a carboxyl group, an ester group, an ether group and a halogen atom or a hydrocarbon residue containing the above functional group, and they may be the same or different.

(2) Case where "p" is 1:

$X^1$, $X^2$ and $X^3$ are the same as in the case where "p" is 0. $X^4$ represents as well, as is the case with $X^1$ to $X^3$, at least one element selected from "N" (nitrogen), "O" (oxygen) and "S" (sulfur), and from the viewpoints of a stability of the compound, a deterioration resistance of a product containing the compound and protecting the catalyst from being poisoned, $X^1$ to $X^4$ are preferably either element selected from "N" or "O".

The same conditions as in the case where "p" is 0 apply to $R^1$ and $R^2$, and the same conditions as those of $R^1$ and $R^2$ apply to $R^3$ and $R^4$.

$R^1$ to $R^4$ may be the same or different, and $R^1$ and $R^2$ and $R^3$ and $R^4$ are not a hydrogen atom at the same time.

The same conditions as in the case where "p" is 0 apply to $Y^1$ and $Y^2$. The same conditions as those of $Y^1$ and $Y^2$ apply to $Y^3$.

The same conditions as in the case where "p" is 0 apply to m, n, "x", "y" and "v". The term "w" is an integer of 0 to 3, and from the viewpoint of a stability of the compound, preferably, when "m" and "n" are 0, "w" is 1 or 2; and when either of "m" and "n" is 1 and the other is 0, "w" is 0.

The term "k" is an integer of 0 to 3; "u" is an integer of 0 to 4; and "t" is an integer of 0 to 3. From the viewpoint of a stability of the compound, preferably, when "k" is 0, "u" is 3 or 4; when k is 1, "u" is any one of 0, 1 and 2; when "k" is 2, "u" is 0. More preferably, when "k" is 0, "u" is 3 or 4; when "k" is 1 and when "u" is 0, "t" is 2 or 3; when "k"=1 and when "u" is 1, "t" is 1 or 2; when "k" is 1 and when "u" is 2, "t" is 0 or 1; and when "k" is 2 and when "u" is 0, "t" is 1.

The same conditions as in the case where "p" is 0 apply to $X^1$ and $X^3$, and when $X^4$ is "N", one of two bonding sites in "N" is occasionally a double bond. When one bonding site is a single bond or both bonding sites are single bonds, shown is the state that one group selected from $R^3$, $R^4$, $Y^2$ and hydrogen is bonded to the bonding site.

When "p" is 1, "C" in the general formula (I) is the same as in the case where "p" is 0. All of "C" in the structural unit (II) represent a carbon element, and either one of two bonding sites in respective "C" is occasionally a double bond. Shown is the state that in both of a case where one bonding site of "C" is a double bond and a case where it does not have a double bond, expression of bonding sites of remaining one or two single bonds is abbreviated and that two groups selected from $R^3$, $R^4$, $Y^3$ and hydrogen are bonded to the abbreviated bonding sites.

The heterocyclic compound represented by the general formula (I) is a reaction product obtained by reacting, for example, (a) a compound such as pyridine and the like which is a fundamental skeleton of a heterocycle and a derivative thereof with (b) a compound having an alkyl group having 6 to 30 carbon atoms, an alkenyl group, an amide group, a cycloalkyl group or an aryl group in a mole ratio (a):(b) of 1:5 to 5:1, preferably 1:2 to 2:1.

Controlling the mole ratio (a):(b) to 1:5 or more and 5:1 or less prevents an active ingredient amount of the additive of the present invention from being decreased and prevents it from having to be added in a large amount in order to exhibit the friction reducing effect.

The reaction of (a) with (b) is carried out at room temperature to 200° C., preferably about 50 to 150° C. The reaction may be carried out under the absence or presence of a catalyst.

In carrying out the reaction, a solvent, for example, an organic solvent such as hexane, toluene, xylene, THF, DMF and the like can be used as well.

In the heterocyclic compound represented by the general formula (I), (a) the compound such as pyridine and the like which is a fundamental skeleton of a heterocycle and the derivative thereof include pyridines such as pyridine, methylpyridine, dimethylpyridine, ethylpyridine, ethylmethylpyridine, viylpyridine, aminopyridine, oxypyridine and the like; pyrroles such as pyrrole, methylpyrrole, ethylpyrrole, aminopyrrole, pyrrolecarboxylic acid and the like; pyrimidines such as 2-aminouracil, 5-methylcytosine, uracil, thimine and the like; pyrazoles such as benzopyrazole, methylpyrazole, ethylpyrazole, aminopyrazole and the like; pyridazines such as pyridazine, methylpyridazine, ethylpyridazine and the like; indazoles such as 6-aminoindazole, indazole and the like; pyrazines such as methylpyrazine, ethylpyrazine, aminopyrazine and the like; triazines such as 1,2,3-benzotriazine, aminotriazine and the like; triazoles such as 3,5-diamino-1,2,4-triazole, 3-amino-1,2,4-triazole and the like; imidazolidines such as 5,5-dimethylhydantoin, methylimidazolidine, ethylimidazolidine, aminoimidazolidine and the like; glycerol formal; benzotriazoles such as methylbenzotriazole, ethylbenzotriazole, aminobenzotriazole and the like; tetrazoles such as methyltetrazole, aminotetrazole and the like; oxazoles such as methyloxazole, aminooxazole and the like; oxadiazoles such as methyloxadiazole, aminooxadiazole and the like; thiazoles such as methylthiazole, aminothiazole and the like; thiadiazoles such as methylthiadiazole, aminothiadiazole and the like; furans; dioxanes; pyrans; thiophenes and derivatives thereof.

They may be compounds obtained by adding substituents such as a hydrocarbon group or an amino group, an amide group, a hydroxyl group, a carbonyl group, an aldehyde group, a carboxyl group, an ester group, an ether group, a halogen atom and a hydrocarbon group substituted with the above groups or a hydrocarbon residue containing the above functional group to the compound (a).

The examples of the hydrocarbon group include methyl, ethyl, propyl, butyl, pentyl, hexyl and the like.

The compound (b) includes higher fatty acid halides such as oleic chloride, heptylundecanoic chloride, tridecanoic chloride, isostearic chloride, polyisobutanoic (for example, Mw=350) chloride and oleic bromide, fatty acid anhydrides such as oleic anhydride, heptylundecanoic anhydride, tridecanoic anhydride and isostearic chloride, aliphatic halides such as oleyl bromide, heptylundecyl bromide, trtidecyl bromide and isostearyl bromide, aliphatic tosylates such as oleyl tosylate, heptylundecyl tosylate, tridecyl tosylate and isostearyl tosylate and aliphatic mesylates such as oleyl mesylate, heptylundecyl mesylate, tridecyl mesylate and isostearyl mesylate. They may be used alone or in a mixture of two or more kinds thereof. The other synthetic methods therefor include a method in which the heterocyclic compound is obtained by reacting amidines with glyoxals or by reacting ethylenediamines with carboxylic acids.

A cyclic structure part in the case where "p" is 0 in the heterocyclic compound represented by the general formula (I) or two cyclic structure parts in the case where "p" is 1 originate in the compound (a) described above. At least one of $Y^1$ and $Y^2$ originates in the compound (b).

The fundamental skeleton of the heterocyclic compound represented by the general formula (I) is a saturated or unsaturated compound in which the total of the number of "N" (nitrogen) and/or "O" (oxygen) and/or "S" (sulfur) in one ring is 1 to 3.

The lubricating oil composition is obtained by mixing the lubricating base oil with various additives for lubricating oils containing, if necessary, the heterocyclic compound represented by the general formula (I) which is the additive for lubricating oils of the present invention obtained in the manner described above.

The various additives for lubricating oils include the following compounds (a preferred content and a more preferred content in the total amount of the lubricating oil composition containing the lubricating base oil described later are described in a parenthesis).

They include viscosity index improving agents of a polymethacrylate base and the like (preferably 1 to 12, more preferably 1 to 4% by mass), corrosion inhibitors of a benzotriazole base and the like (preferably 0.01 to 3, more preferably 0.01 to 1.5% by mass), antioxidants of alkylated diphenylamine and the like (preferably 0.01 to 5, more preferably 0.01 to 1.5% by mass), dispersants of polybutenylsuccinic imide and the like (preferably 0.1 to 10, more preferably 0.1 to 5% by mass), fluidity improving agents for lubricating oil (preferably 0.01 to 2, more preferably 0.01 to 1.5% by mass), rust preventives of an alkenylsuccinic ester base and the like (preferably 0.1 to 6, more preferably 0.1 to 3% by mass), pour point depressants of polymethacrylate and the like (preferably 0.01 to 1.5, more preferably 0.01 to 0.5% by mass), defoaming agents (preferably 0.001 to 0.1, more preferably 0.001 to 0.01% by mass), abrasion preventives of a phosphorous ester base and the like (preferably 0.001 to 5, more preferably 0.001 to 1.5% by mass), seal swelling agents (preferably 0.1 to 8, more preferably 0.1 to 4% by mass), friction controlling agents of fatty acid amide and the like (preferably 0.01 to 3, more preferably 0.01 to 1.5% by mass) and the like.

The additive for lubricating oils of the present invention is used in a content of 0.01 to 10% by mass, preferably 0.05 to 5% by mass and more preferably 0.1 to 2% by mass based on the total amount including an amount of the lubricating base oil. Controlling the content to 0.01% by mass or more makes it possible to exhibit the friction reducing effect, and controlling the content to 10% by mass or less makes it possible to avoid an increase in the cost and reduce intrinsic characteristic endowed to the lubricating base oil.

The lubricating base oil shall not be specifically restricted, and various lubricating base oils of a mineral oil base and a synthetic base can be used.

The mineral oil based-lubricating base oils include, to be specific, hydrocarbon oils obtained by refining lubricating oil fractions obtained by distilling crude oils under atmospheric pressure and reduced pressure by subjecting them to suitably combined refining treatment of debitumen by solvents, extraction by solvents, hydrocracking, dewaxing by solvents, catalytic dewaxing, hydrogenation refining, washing with sulfuric acid, clay treatment and the like.

In this respect, all of lubricating oils such as paraffin based-mineral oils, naphthene based-mineral oils, aromatic mineral oils and the like can be used as the hydrocarbon oils.

Further, capable of being used as the lubricating base oils of a synthetic base are, to be specific, phenyl ether based-synthetic oils such as polyphenyl ether, polyolefin based-synthetic oils such as poly-α-olefin (polybutene, 1-octene oligomers, 1-decene oligomers and the like or hydrogenated products thereof) and the like, benzene based-synthetic oils such as alkylbenzene and the like, naphthalene based-synthetic oils such as alkylnaphthalene and the like, ester based-synthetic oils such as diesters (ditridecyl glutarate, di-2-ethylhexyl adipate, diisodecyl adipate, ditridecyl adipate, di-2-ethylhexyl sebacate and the like), polyol esters (trimethylolpropane capriate, trimethylolpropane pelargonate, pentaerythritol 2-ethylhexanoate, pentaerythritol pelargonate and the like), glycol based-synthetic oils such as polyoxyalkylene glycol and the like, ether based-synthetic oils such as polyphenyl ether and the like and silicone based-synthetic oils such as silicone fluorinated oils and the like. The above base oils may be used alone or in a mixture of two or more kinds thereof.

When the lubricating oil composition obtained by adding the additive for lubricating oils of the present invention to the lubricating base oil is used for internal combustion engines and driving systems under a wet condition, it exhibits notably a friction reducing effect and works primarily as a friction reducing agent.

Parts of low friction slide members having a diamond-like carbon (DLC) film on a part of sliding parts to which the additive for lubricating oils of the present invention and the lubricating oil composition containing the same are applied include the following examples:

In an internal combustion engine, they include piston rings and cylinders, piston skirts and cylinders, piston pins and connecting rods, piston pins and bushes, cams and shims, cams and locker arms, cam diurnals and cam shafts, needle bearing parts of roller locker arms, locker arms and locker shafts, roller tappets and cams, pins and connecting rods of crank shafts, bearing parts of crank shafts, plates and pins constituting timing chains, timing chains and sprockets, shoes and chains for timing chain guides, shoes and chains for tensioners of timing chains, valve sheet surfaces and valve face surfaces, stem surfaces and stem guides of valves, stem surfaces and stem seals, stem ends and valve lifters, outer gears and inner gears of oil pumps, outer rotors and inner rotors of oil pumps, rolling parts of turbo chargers, thrust bearing parts of turbo chargers and the like.

In an automatic transmission, they include teeth surfaces of gears, roller bearing parts of gears, driven gears and driving gears of oil pumps and the like.

An infinitely variable transmission is an automatic transmission which is infinitely variable, and in the present specification, it means a infinitely variable transmission in which a fixed pulley and a movable pulley are mounted on a drive shaft and a driven shaft and in which a motive power is transmitted between the above two pulleys via a metal belt or a metal chain to thereby vary a speed at a single step. In a infinitely variable transmission, they include teeth surfaces of gears, roller bearing parts of gears, driven gears and driving gears of oil pumps, steel blocks and steel bands of metal belts, blocks and pins of metal chains, pins and links, blocks and links and the like.

In a manual transmission, they include teeth surfaces of gears, roller bearing parts of gears, shift fork nail parts and sleeves, heads and inner levers of shift forks and the like.

In a final reduction gear, they include teeth surfaces of gears, roller bearing parts of gears, seal parts of input and output shafts and the like.

In a shock absorber for vehicles, they include piston rods and bushes, piston rods and shoes and the like.

In an electric power steering, they include worm wheels, worms and the like.

Principal types of a refrigerant compressor include a reciprocal type, a swash plate type, a vane rotary type, a rolling piston type and a scroll type. In the reciprocal type, they include piston rings and cylinders, pistons and cylinders, pistons and piston pins, piston pins and connecting rods, connecting rods and crank shafts, roller bearing parts of crank shafts and the like. In the swash plate type, they include swash plates and shoes, spherical seats and shoes of pistons, thrust roller bearing parts of shafts, diurnal roller bearing parts of shafts, pistons and cylinders, piston rings and cylinders and the like. In the vane rotary type, they include vane tips and cylinders, vanes and rotors, vane side faces and cylinders, rotors and cylinders and the like.

In the rolling piston type, they include vanes and rolling pistons, rolling pistons and cylinders, vanes and cylinders and the like.

In the scroll type, they include lap edges and flat plates, roller bearing parts of shafts, Oldham's rings and circling scroll rings in the case of an Oldham's mechanism, Oldham's rings and frames, driving bearings in the case of a pin crank mechanism, driving pins and eccentric bushes and the like.

In a hydraulic pump and motor, they include cylinders and pistons, pistons and cams in a rodless type of an axial type, pistons and slippers, cams and slippers, rods and pistons in a piston of a rod type, rods and roller bearing parts and the like.

Counterpart members of the low friction slide members having a diamond-like carbon (DLC) film shall not specifically be restricted and include, for example, iron based-members, aluminum alloy members and organic materials such as resins and rubber materials.

In this regard, the low friction slide members having a DLC film described above has a DLC film on a surface, and DLC constituting the above film comprises primarily a carbon element and is amorphous, wherein a bonding form between carbons comprises both of a diamond structure (SP3 bonding) and a graphite structure (SP2 bonding).

To be specific, it includes a-C (amorphous carbon) comprising a carbon element alone, a-C:H (hydrogen amorphous carbon) containing hydrogen and MeC containing partially a metal element such as titanium (Ti), molybdenum (Mo) and the like, and a low friction slide member having a DLC film comprising an a-C:H base material containing hydrogen is suited to the additive for lubricating oils of the present invention.

On the other hand, a constituent material for the iron based-member includes, for example, carburized steels SCM420, ScR420 and the like.

A hypoeutectic aluminum alloy containing 4 to 20% by mass of silicon and 1.5 to 5.0% by mass of copper or a hypereutectic aluminum alloy is preferably used as a constituent material for the aluminum alloy member. To be specific, it includes AC2A, AC8A, ADC12, ADC14 (all based on JIS) and the like.

The respective surfaces roughness of the low friction slide member having a DLC film and the iron based-member or the low friction slide member having a DLC film and the aluminum alloy member are suitably 0.1 μm or less in terms of an arithmeric average roughness Ra from the viewpoint of safety of sliding. Controlling the surfaces roughness to 0.1 μm or less makes it difficult to form local scuffing and makes it possible to control an increase in the friction coefficient. Further, the low friction slide member having a DLC film described above has preferably a surface hardness of Hv 1000 to 3500 in terms of a micro Vickers hardness (98 mN load) and a thickness of 0.3 to 2.0 μm. If a surface hardness and a thickness of the low friction slide member having a DLC film fall in the ranges described above, abrasion and peeling are prevented.

On the other hand, the iron based-member described above has preferably a surface hardness of HRC 45 to 60 in terms of a Rockwell hardness (C scale). In this case, a durability of the DLC film can be maintained, as is the case with a cam follower member, even on a sliding condition under a high surface pressure of about 700 MPa, and therefore it is effective. The aluminum alloy member described above has preferably a surface hardness of HB 80 to 130 in terms of a Brinell hardness. If the iron based-member has a surface hardness of HRC 45 or more, it can be prevented from buckling and peeling under a high surface pressure. Also, if a surface hardness of the aluminum alloy member falls in the range described above, the aluminum alloy member can be inhibited from being abraded.

Polyamideimide, PTEF and the like as the resin and NBR, HNBR, EPDM, CR and the like as the rubber can be used as the counterpart materials. The base material for the low friction slide member having a DLC film shall by no means be restricted, and any materials of metals, resins, rubber materials and the like can be used.

EXAMPLES

The present invention is explained below in further details with reference to the examples of the present invention, but the present invention is not restricted to these examples.

Synthetic Example 1

A flask of 500 ml was charged with 5.0 g (0.05 mole) of 3,5-diamino-1,2,4-triazole, 5.3 g (0.053 mole) of triethylamine and 200 ml of THF, and the mixture was stirred while refluxing. Oleic chloride 15.0 g (0.05 mole) dissolved in 50 ml of THF was dropwise added thereto to carry out reaction for 4 hours. The reaction mixture was filtrated, and THF was removed by distillation. Then, the residue was dissolved in 200 ml of toluene and washed with water. The solution was dried on magnesium sulfate, and then toluene was removed by distillation to obtain a heterocyclic compound. A yield of the heterocyclic compound thus obtained was 16 g.

In the structural general formula of the principal component of the heterocyclic compound obtained above, "p" in the general formula (I) is 0, and both of "m" and "n" are 1; all of $X^1$, $X^2$ and $X^3$ are "N"; any one of "x", "y" and "v" is 0, and the other two are 1; one of $R^1$ and $R^2$ is an oleic amide group, and the other is hydrogen; $Y^1$ is an amino group, and $Y^2$ is hydrogen. This heterocyclic compound is referred to as "Additive 1".

Synthetic Example 2

The reaction was carried out in the same manner as in Synthetic Example 1, except that 4.2 g (0.05 mole) of 3-amino-1,2,4-triazole was used in place of 3,5-diamino-1,2,4-triazole. A yield of the heterocyclic compound thus obtained was 16 g.

In the structural general formula of the principal component of the heterocyclic compound obtained above, "p" in the general formula (I) is 0, and both of "m" and "n" are 1; all of $X^1$, $X^2$ and $X^3$ are "N"; any one of "x", "y" and "v" is 0, and the other two are 1; one of $R^1$ and $R^2$ is an oleic amide group, and the other is hydrogen; and $Y^1$ and $Y^2$ are hydrogen. This heterocyclic compound is referred to as "Additive 2".

Synthetic Example 3

The reaction was carried out in the same manner as in Synthetic Example 1, except that 6.7 g (0.05 mole) of 6-aminoindazole was used in place of 3,5-diamino-1,2,4-triazole. A yield of the heterocyclic compound thus obtained was 17 g.

In the structural general formula of the principal component of the heterocyclic compound obtained above, "p" in the general formula (I) is 1; "m" is 1, and "n" is 0; "k" is 0; $X^1$ and $X^3$ are "N"; "x" is 0; "v" is 1; "w" is 0: "u" is 4; $R^1$ and $R^2$ are hydrogen; one of $R^3$ and $R^4$ is an oleic amide group, and the other is hydrogen; and $Y^1$, $Y^2$ and $Y^3$ are hydrogen. This heterocyclic compound is referred to as "Additive 3".

Synthetic Example 4

The reaction was carried out in the same manner as in Synthetic Example 1, except that 15.1 (0.05 mole) of heptylundecanoic chloride was used in place of oleic chloride. A yield of the heterocyclic compound thus obtained was 17 g.

In the structural general formula of the principal component of the heterocyclic compound obtained above, "p" in the general formula (I) is 0, and both of "m" and "n" are 1; all of $X^1$, $X^2$ and $X^3$ are "N"; any one of "x", "y" and "v" is 0, and the other two are 1; one of $R^1$ and $R^2$ is a heptylundecanoic amide group, and the other is hydrogen; and $Y^1$ and $Y^2$ are hydrogen. This heterocyclic compound is referred to as "Additive 4".

Synthetic Example 5

The reaction was carried out in the same manner as in Synthetic Example 1, except that 6.4 g (0.05 mole) of 2-aminouracil was used in place of 3,5-diamino-1,2,4-triazole.

A yield of the heterocyclic compound thus obtained was 17 g.

In the structural general formula of the principal component of the heterocyclic compound obtained above, a mixture of a compound in which "p" in the general formula (I) is 0; "m" is 1, and "n" is 0; "v" is 3; $X^1$ and $X^3$ each are "N"; "x" is 1; one of $R^1$ and $R^2$ is an oleic amide group, and the other is hydrogen; and $Y^1$ and $Y^2$ are a hydroxyl group and a compound in which one of $R^1$ and $R^2$ is an oleyl ether group, and the other is hydrogen; $Y^1$ is a hydroxyl group, and $Y^2$ is an amino group. This heterocyclic compound is referred to as "Additive 5".

Synthetic Example 6

The reaction was carried out in the same manner as in Synthetic Example 1, except that 6.4 g (0.05 mole) of 5,5-dimethylhydatoin was used in place of 3,5-diamino-1,2,4-triazole. A yield of the heterocyclic compound thus obtained was 16 g.

In the structural general formula of the principal component of the heterocyclic compound obtained above, "p" in the general formula (I) is 0; "m" is 1, and "n" is 0; $X^1$ and $X^3$ each are N; "x" is 1; "v" is 2; one of $R^1$ and $R^2$ is an oleic amide group, and the other is hydrogen; two $Y^1$ are a carbonyl group, and two $Y^2$ are methyl group. This heterocyclic compound is referred to as "Additive 6".

Synthetic Example 7

The reaction was carried out in the same manner as in Synthetic Example 1, except that 5.2 g (0.05 mole) of glycerol formal was used in place of 3,5-diamino-1,2,4-triazole. A yield of the heterocyclic compound thus obtained was 15 g.

In the structural general formula of the principal component of the heterocyclic compound obtained above, "p" in the general formula (I) is 0; "m" is 1, and "n" is 0; $X^1$ and $X^3$ are "O"; "x" is 3; "v" is 1; one of $R^1$ and $R^2$ is an oleic ether group, and the other is hydrogen; and $Y^1$ and $Y^2$ are hydrogen. This heterocyclic compound is referred to as "Additive 7".

Synthetic Example 8

The reaction was carried out in the same manner as in Synthetic Example 1, except that 7.1 g (0.05 mole) of kojic acid was used in place of 3,5-diamino-1,2,4-triazole. A yield of the heterocyclic compound thus obtained was 16 g.

In the structural general formula of the principal component of the heterocyclic compound obtained above, a mixture of a compound in which "p" in the general formula (I) is 0; "m" and "n" are 0; $X^3$ is "O"; "v" is 5; one of $R^1$ and $R^2$ is an oleyl methyl ether group, and the other is hydrogen; $Y^1$ is a hydroxyl group, and $Y^2$ is a carbonyl group and a compound in which one of $R^1$ and $R^2$ is an oleyl ether group, and the other is hydrogen; $Y^1$ is hydroxymethyl group, and $Y^2$ is a carbonyl group. This heterocyclic compound is referred to as "Additive 8".

Synthetic Example 9

The reaction was carried out in the same manner as in Synthetic Example 1, except that 24.3 (0.05 mole) of tridecanoic chloride was used in place of oleic chloride. A yield of the heterocyclic compound thus obtained was 26 g.

In the structural general formula of the principal component of the heterocyclic compound obtained above, "p" in the general formula (I) is 0, and both of "m" and "n" are 1; all of $X^1$, $X^2$ and $X^3$ are "N"; any one of "x", "y" and "v" is 0, and the other two are 1; one of $R^1$ and $R^2$ is a tridecanoic amide group, and the other is hydrogen; $Y^1$ is an amino group, and $Y^2$ is hydrogen. This heterocyclic compound is referred to as "Additive 9".

Synthetic Example 10

The reaction was carried out in the same manner as in Synthetic Example 1, except that 20.7 (0.05 mole) of polyisobutanoic (Mw=350) chloride was used in place of oleic chloride. A yield of the heterocyclic compound thus obtained was 23 g.

In the structural general formula of the principal component of the heterocyclic compound obtained above, "p" in the general formula (I) is 0, and both of "m" and "n" are 1; all of $X^1$, $X^2$ and $X^3$ are "N"; any one of "x", "y" and "v" is 0, and the other two are 1; one of $R^1$ and $R^2$ is a polyisobutanoic amide group, and the other is hydrogen; $Y^1$ is an amino group, and $Y^2$ is hydrogen. This heterocyclic compound is referred to as "Additive 10".

Synthetic Example 11

A flask of 500 ml was charged dropwise with 1.3 g (0.055 mole) of NaH and 100 ml of DMF, and 5.0 g (0.05 mole) of 3,5-diamino-1,2,4-triazole dissolved in 100 ml of DMF was dropwise added thereto to carry out reaction at 100° C. for 2 hours, followed by adding dropwise 16.6 g (0.055 mole) of oleil bromide to carry out reaction at 100° C. for 4 hours. DMF was removed by distillation, and then the residue was dissolved in 200 ml of toluene and washed with water. The solution was dried on magnesium sulfate, and then toluene was removed by distillation to obtain a heterocyclic compound. A yield of the heterocyclic compound thus obtained was 15 g.

In the structural general formula of the principal component of the heterocyclic compound obtained above, "p" in the general formula (I) is 0, and both of "m" and "n" are 1; all of $X^1$, $X^2$ and $X^3$ are "N"; any one of "x", "y" and "v" is 0, and the other two are 1; one of $R^1$ and $R^2$ is an oleyl group, and the other is hydrogen; and both of $Y^1$ and $Y^2$ are an amino group. This heterocyclic compound is referred to as "Additive 11".

Synthetic Example 12

The reaction was carried out in the same manner as in Synthetic Example 11, except that 4.2 g (0.05 mole) of 3-amino-1,2,4-triazole was used in place of 3,5-diamino-1,2, 4-triazole. A yield of the heterocyclic compound thus obtained was 14 g.

In the structural general formula of the principal component of the heterocyclic compound obtained above, "p" in the general formula (I) is 0, and both of "m" and "n" are 1; all of $X^1$, $X^2$ and $X^3$ are "N"; any one of "x", "y" and "v" is 0, and the other two are 1; one of $R^1$ and $R^2$ is an oleyl group, and the other is hydrogen; $Y^1$ is an amino group, and $Y^2$ is hydrogen. This heterocyclic compound is referred to as "Additive 12".

Synthetic Example 13

The reaction was carried out in the same manner as in Synthetic Example 11, except that 6.7 g (0.05 mole) of 6-aminoindazole was used in place of 3,5-diamino-1,2,4-triazole. A yield of the heterocyclic compound thus obtained was 16 g.

In the structural general formula of the principal component of the heterocyclic compound obtained above, "p" in the general formula (I) is 1; "m" is 1, and "n" is 0; "k" is 0; $X^1$ and $X^3$ are "N"; "x" is 0; "v" is 1; "w" is 0: "u" is 4; one of $R^1$ and $R^2$ is an oleyl group, and the other is hydrogen; $R^3$ and $R^4$ are hydrogen; and $Y^1$ and $Y^2$ are hydrogen, and $Y^3$ is an amino group. This heterocyclic compound is referred to as "Additive 13".

Synthetic Example 14

A flask of 500 ml was charged dropwise with NaH 1.3 g (0.055 mole) and the compound 16.8 g (0.05 mole) obtained in Synthetic Example 11 which was dissolved in 100 ml of xylene to react them at 100° c. for 2 hours. Then, 6.9 g (0.055 mole) of 2-boromoethanol was dropwise added thereto and reacted at 100° c. for 4 hours. The reaction product was washed with water and dried, and then xylene was removed by distillation to obtain a heterocyclic compound. A yield of the heterocyclic compound thus obtained was 22 g.

In the structural general formula of the principal component of the heterocyclic compound obtained above, "p" in the general formula (I) is 0, and both of "m" and "n" are 1; all of $X^1$, $X^2$ and $X^3$ are "N"; any one of "x", "y" and "v" is 0, and the other two are 1; one of $R^1$ and $R^2$ is an oleyl group, and the other is hydrogen; $Y^1$ is a hydroxyethylamino group, and $Y^2$ is an amino group. This heterocyclic compound is referred to as "Additive 14".

Synthetic Example 15

A flask of 500 ml was charged with 5.0 g (0.05 mole) of 3,5-diamino-1,2,4-triazole, 10.9 g (0.05 mole) of di-t-butyl pyrocarbonate, 5.5 g (0.055 mole) of triethylamine and 100 ml of DMF, and they were reacted at 60° C. for one hour to obtain a reaction mixture A.

On the other hand, another flask of 500 ml was charged with 1.3 g (0.055 mole) of NaH and 100 ml of DMF. The reaction mixture A described above was dropwise added thereto and reacted at 100° C. for 2 hours to obtain a reaction mixture B. Then, 16.6 g (0.05 mole) of oleyl bromide was dropwise added to the reaction mixture B and reacted at 100° C. for 4 hours. DMF was removed by distillation, and then the residue was dissolved in 200 ml of toluene and reacted at 60° C. for 2 hours under an acid condition in an HCl aqueous solution. Then, the solution was neutralized with a NaOH aqueous solution, and the toluene layer was washed with water. Subsequently, the toluene layer was dried on magnesium sulfate, and toluene and light components were removed by distillation to obtain 15 g of a heterocyclic compound.

In the structural general formula of the principal component of the heterocyclic compound obtained above, "p" in the general formula (I) is 0, and both of "m" and "n" are 1; all of $X^1$, $X^2$ and $X^3$ are "N"; any one of "x", "y" and "v" is 0, and the other two are 1; one of $R^1$ and $R^2$ is an oleylamino group, and the other is hydrogen; $Y^1$ is an amino group, and $Y^2$ is hydrogen. This heterocyclic compound is referred to as "Additive 15".

Synthetic Example 16

The reaction was carried out in the same manner as in Synthetic Example 14, except that 6.8 g (0.05 mole) of 2-boromoethylamine was used in place of 2-boromoethanol. A yield of the heterocyclic compound thus obtained was 22 g.

In the structural general formula of the principal component of the heterocyclic compound obtained above, "p" in the general formula (I) is 0, and both of "m" and "n" are 1; all of $X^1$, $X^2$ and $X^3$ are "N"; any one of "x", "y" and "v" is 0, and the other two are 1; one of $R^1$ and $R^2$ is an oleyl group, and the other is hydrogen; $Y^1$ is an aminoethylamino group, and $Y^2$ is an amino group. This heterocyclic compound is referred to as "Additive 16".

Synthetic Example 17

A flask of 500 ml was fed with 12.1 g (0.11 mole) of aminoquanidine.hydrochloride, 28.2 g (0.1 mole) of oleic acid, 200 ml of xylene and 110 ml of a NaOH aqueous solution of 1M (mole/liter), and they were reacted at 150° C. for 2 hours under nitrogen flow while stirring. Then, the xylene layer was separated and washed with water. A flask of 500 ml was fed with the xylene layer obtained after washed with water and heated to 160° C. under nitrogen flow while removing xylene by distillation to carry out reaction for 2 hours under stirring, and then xylene was removed by distillation under reduced pressure to obtain 27 g of a heterocyclic compound.

In the structural general formula of the principal component of the heterocyclic compound obtained above, "p" in the general formula (I) is 0, and both of "m" and "n" are 1; all of $X^1$, $X^2$ and $X^3$ are "N"; any one of "x", "y" and "v" is 0, and the other two are 1; one of $R^1$ and $R^2$ is a 8-heptadecenyl group, and the other is hydrogen; one of $Y^1$ and $Y^2$ is an amino group, and the other is hydrogen. This heterocyclic compound is referred to as "Additive 17".

Examples 1 to 17

A mineral oil of 100 neutral fraction was blended with 5.5% by mass of a viscosity index improving agent, 0.3% by mass of a fluidity improving agent, 0.3% by mass of an antioxidant, 5% by mass of an ashless dispersant, 1.2% by mass of a metal based-detergent, 1% by mass of ZnDTP and 1% by mass of "Additives 1 to 17" each based on the whole mass to prepare lubricating oil compositions. The performances of the respective lubricating oil compositions were evaluated by means of a reciprocating friction tester (Test method 1) and a SRV tester (Test method 2).

Results obtained in Examples 1 to 8 are shown in Table 1, and results obtained in Examples 9 to 17 are shown in Table 2. Only the lubricating oil compositions obtained in Examples 1 and 8 were evaluated by the Test method 1 and the Test method 2.

Examples 18 to 20

The mineral oil of 100 neutral fraction was blended with each 1% by mass of "Additives 1, 8 and 12" based on the whole mass to prepare lubricating oil compositions. The performances of the respective lubricating oil compositions were evaluated by means of the reciprocating friction tester (Test method 1) and the SRV tester (Test method 2). The results thereof are shown in Table 3.

Comparative Example 1

The mineral oil of 100 neutral fraction was blended with 5.5% by mass of the viscosity index improving agent, 0.3% by mass of the fluidity improving agent, 0.3% by mass of the antioxidant, 5% by mass of the ashless dispersant, 1.2% by mass of the metal based-detergent and 1% by mass of ZnDTP each based on the whole mass to prepare a lubricating oil composition, and it was used to evaluate the performances thereof by means of the reciprocating friction tester (Test method 1) and the SRV tester (Test method 2). The results thereof are shown in Table 2.

Comparative Example 2

The mineral oil of 100 neutral fraction was blended with 5.5% by mass of the viscosity index improving agent, 0.3% by mass of the fluidity improving agent, 0.3% by mass of the antioxidant, 5% by mass of the ashless dispersant, 1.2% by mass of the metal based-detergent, 1% by mass of ZnDTP and 1% by mass of "an additive 18" (commercially available oleic amide) each based on the whole mass to prepare a lubricating oil composition to prepare a lubricating oil composition for comparison, and it was evaluated by means of the reciprocating friction tester (Test method 1) and the SRV tester (Test method 2). The results thereof are shown in Table 2.

Comparative Example 3

The mineral oil of 100 neutral fraction was blended with 5.5% by mass of the viscosity index improving agent, 0.3% by mass of the fluidity improving agent, 0.3% by mass of the antioxidant, 5% by mass of the ashless dispersant, 1.2% by mass of the metal based-detergent, 1% by mass of ZnDTP and 1% by mass of "an additive 19" (commercially available glycerol monooleate) each based on the whole mass to prepare a lubricating oil composition for comparison, and it was evaluated by means of the reciprocating friction tester (Test method 1) and the SRV tester (Test method 2). The results thereof are shown in Table 2.

Comparative Example 4

The mineral oil of 100 neutral fraction was used to evaluate performances thereof by means of the reciprocating friction tester (Test method 1) and the SRV tester (Test method 2). The results thereof are shown in Table 3.

Comparative Example 5

The mineral oil of 100 neutral fraction was blended with 0.4% by mass of "an additive 20" (commercially available MoDTC) and 0.5% by mass of "an additive 21" (commercially available ZnDTP) each based on the whole mass to prepare a lubricating oil composition for comparison, and the performances thereof were evaluated by means of the reciprocating friction tester (Test method 1) and the SRV tester (Test method 2). The results thereof are shown in Table 3.

<Test Methods and Test Conditions>
1. Test method 1 (Table 1 and Table 2)
   Tester: reciprocating friction tester
   Test Piece:
   Friction test *1) test plate: SCM415, test ball: SUJ-2 (½ inch)
   Friction test *2) test plate: A1050, test ball: SUJ-2 (½ inch)
   Test conditions: oil temperature: 100° C., sliding velocity: 3 mm/sec, load: 200 g
   Judge: friction coefficient
2. Test Method 1 (Table 3)
   Tester: SRV tester
   Test piece: test plate SCM420 material coated thereon with hydrogen-free DLC
   SCM420 material coated thereon with DLC containing 20 atom % of hydrogen Test cylinder FCD700
   Test conditions: oil temperature: 80° C., amplitude: 1.5 mm, frequency: 50 Hz, load: 400N
   Judge:
   Friction coefficient *1) material coated thereon with hydrogen-free DLC was used for a test plate
   Friction coefficient *2) material coated thereon with DLC containing 20 atom % of hydrogen was used for a test plate

TABLE 1

|  | Example | | | | | | | |
|---|---|---|---|---|---|---|---|---|
|  | 1 | 2 | 3 | 4 | 5 | 6 | 7 | 8 |
| Mineral oil (% by mass) | 85.7 | 85.7 | 85.7 | 85.7 | 85.7 | 85.7 | 85.7 | 85.7 |
| Additive 1 | 1 | | | | | | | |
| Additive 2 | | 1 | | | | | | |
| Additive 3 | | | 1 | | | | | |
| Additive 4 | | | | 1 | | | | |
| Additive 5 | | | | | 1 | | | |
| Additive 6 | | | | | | 1 | | |
| Additive 7 | | | | | | | 1 | |
| Additive 8 | | | | | | | | 1 |
| Friction coefficient *1) | 0.106 | 0.106 | 0.110 | 0.131 | 0.133 | 0.128 | 0.116 | 0.127 |
| Friction coefficient *2) | 0.128 | | | | | | | 0.135 |

*1) test plate SCH415, test ball: SUJ-2 (½ inch)
*2) test plate A1050, test ball: SUJ-2 (½ inch)

TABLE 2

|  | Example | | | | | | | | | Comparative Example | | |
|---|---|---|---|---|---|---|---|---|---|---|---|---|
|  | 9 | 10 | 11 | 12 | 13 | 14 | 15 | 16 | 17 | 1 | 2 | 3 |
| Mineral oil (% by mass) | 85.7 | 85.7 | 85.7 | 85.7 | 85.7 | 85.7 | 85.7 | 85.7 | 85.7 | 86.7 | 85.7 | 85.7 |
| Additive 9 | 1 | | | | | | | | | | | |
| Additive 10 | | 1 | | | | | | | | | | |

TABLE 2-continued

|  | Example | | | | | | | | | Comparative Example | | |
|---|---|---|---|---|---|---|---|---|---|---|---|---|
|  | 9 | 10 | 11 | 12 | 13 | 14 | 15 | 16 | 17 | 1 | 2 | 3 |
| Additive 11 |  | 1 |  |  |  |  |  |  |  |  |  |  |
| Additive 12 |  |  | 1 |  |  |  |  |  |  |  |  |  |
| Additive 13 |  |  |  | 1 |  |  |  |  |  |  |  |  |
| Additive 14 |  |  |  |  | 1 |  |  |  |  |  |  |  |
| Additive 15 |  |  |  |  |  | 1 |  |  |  |  |  |  |
| Additive 16 |  |  |  |  |  |  | 1 |  |  |  |  |  |
| Additive 17 |  |  |  |  |  |  |  | 1 |  |  |  |  |
| Additive 18 |  |  |  |  |  |  |  |  | 1 |  |  |  |
| Additive 19 |  |  |  |  |  |  |  |  |  |  | 1 |  |
| Friction coefficient *1) | 0.138 | 0.133 | 0.098 | 0.096 | 0.106 | 0.096 | 0.101 | 0.096 | 0.098 | 0.173 | 0.150 | 0.151 |
| Friction coefficient *2) |  |  |  |  |  |  |  |  |  | 0.22 | 0.141 | 0.139 |

*1) test plate SCH415, test ball: SUJ-2 (½ inch)
*2) test plate A1050, test ball: SUJ-2 (½ inch)

TABLE 3

|  | Example | | | Comparative Example | |
|---|---|---|---|---|---|
|  | 18 | 19 | 20 | 4 | 5 |
| Mineral oil (% by mass) | 99.5 | 99.5 | 99.5 | 100 | 99.1 |
| Additive 1 | 0.5 |  |  |  |  |
| Additive 8 |  | 0.5 |  |  |  |
| Additive 12 |  |  | 0.5 |  |  |
| Additive 20 |  |  |  |  | 0.4 |
| Additive 21 |  |  |  |  | 0.5 |
| Friction coefficient *1) | 0.072 | 0.035 | 0.065 | 0.113 | 0.106 |
| Friction coefficient *2) | 0.112 | 0.121 | 0.114 | 0.150 | 0.118 |

*1) test plate (SCM420 material) coated thereon with hydrogen-free DLC, test cylinder FCD700
*2) test plate (SCM420 material) coated thereon with DLC containing 20 atom % of hydrogen, test cylinder FCD700

Addition of the total numeral values of the blend amounts (unit:% by mass) of the mineral oil and the respective additives in Table 1 and Table 2 described above to the numeral values of the blend amounts (total 13.3% by mass) of the other additives such as the viscosity index improving agent and the like makes 100.

It can be found by comparison of the friction coefficients shown respectively in Examples 1 to 17 and Comparative Examples 1 to 3 in Table 1 and Table 2 that the additives lubricating oil of the present invention exhibit more excellent friction reducing effects than those of the conventional products.

Further, it can be found as well by comparison of Examples 18 to 20 with Comparative Examples 4 and 5 in Table 3 that also in the low friction slide members having a diamond-like carbon (DLC) film on a surface, the lubricating oil compositions containing the additives for lubricating oil of the present invention exhibit more excellent friction reducing effects than those of the conventional products.

Industrial Applicability

The lubricating oil compositions obtained by blending the additives for lubricating oil of the present invention with hydrocarbon oils of a mineral oil base and synthetic lubricating base oils or mixtures thereof enhance frictional characteristics of slide parts in internal combustion engines and driving system transmission engines and exhibit an excellent fuel consumption reducing effect. In addition thereto, they are an ashless type and therefore suited as an environmental responsive additive for lubricating oils in the future.

The specific uses of the additives lubricating oil of the present invention include lubricating oils for internal combustion engines, gear oils, roller bearing oils, transmission oils, shock absorber oils, industrial lubricating oils and the like. Further, they can be used also as lubricating oils for internal combustion engines and driving system transmission engines to which low friction slide members coated with various hard thin film materials such as diamond-like carbon (DLC), TiN, CrN and the like and lubricating oils for facilities and working.

What is claimed is:

1. An additive for lubricating oils having a skeleton of 1,2,4-triazole and having at least one group (A) selected from the group consisting of an alkenylamino group having 18 carbon atoms, an alkenylamido group having 18 carbon atoms, an alkenyl group having 17 carbon atoms, and an alkenyl group having 18 carbon atoms, bonded thereto, wherein
    (1) at least one group (A) is bonded to a nitrogen atom in the skeleton of 1,2,4-triazole, or
    (2) at least one amino group in addition to a group (A) is bonded to the skeleton of 1,2,4-triazole and at least one group (A) is bonded to a nitrogen atom in the skeleton of 1,2,4-triazole.

2. The additive for lubricating oils as claimed in claim 1, wherein at least one group (A) is bonded to a nitrogen atom in the skeleton of 1,2,4-triazole.

3. The additive for lubricating oils as claimed in claim 2, wherein group (A) is an oleic amido group, an oleic amine group, an oleyl group, or an 8-heptadecenyl group.

4. The additive for lubricating oils as claimed in claim 1, wherein at least one amino group in addition to a group (A) is bonded to the skeleton of 1,2,4-triazole and at least one group (A) is bonded to a nitrogen atom in the skeleton of 1,2,4-triazole.

5. A friction reducing agent comprising the additive for lubricating oils as claimed in claim 2.

6. A lubricating oil composition comprising the additive for lubricating oils as claimed in claim 2 and a lubricating base oil.

7. A method comprising lubricating an internal combustion engine with the lubricating oil composition as claimed in claim 6.

8. A method comprising lubricating a driving system with the lubricating oil composition as claimed in claim 6.

9. A method comprising lubricating a low friction slide member on a wet condition with the lubricating oil composition as claimed in claim 6.

10. The as claimed in claim 9, wherein the low friction slide member is a member having a diamond-like carbon film on a surface.

11. The method as claimed in claim 10, wherein the diamond-like carbon film comprises an amorphous carbon based-material having a hydrogen content of 30 atom % or less.

12. A low friction slide member which is provided at least on a part of a slide part with a diamond-like carbon film comprising applying and in which the lubricating oil composition as claimed in claim 6 is present on a sliding surface, wherein it is selected from low friction slide members for internal combustion engines, low friction slide members for automatic transmissions, low friction slide members for infinitely variable transmissions, low friction slide members for manual transmissions, low friction slide members for an electric power steering, low friction slide members for shock absorbers for cars, low friction slide members for cooling medium compressors, low friction slide members for hydraulic pumps and low friction slide members for clutch pulleys.

13. An antifriction bearing comprising at least a part of a slide part with a diamond-like carbon film and having the lubricating oil composition as claimed in claim 6 for a sliding surface.

14. A slide bearing comprising at least a part of a slide part with a diamond-like carbon film and having the lubricating oil composition as claimed in claim 6 for a sliding surface.

* * * * *